(12) United States Patent
Dvorak et al.

(10) Patent No.: US 10,096,075 B2
(45) Date of Patent: Oct. 9, 2018

(54) PATIENT COMMUNITY SYSTEM WITH ANONYMIZED ELECTRONIC MEDICAL DATA

(75) Inventors: Carl D. Dvorak, Verona, WI (US); Brian M. Weisberger, Madison, WI (US); Matthew D. Sidney, Fitchburg, WI (US); Janet L. Campbell, Madison, WI (US); Daniel J. Donoghue, Oregon, WI (US); John Ji-hoon Kim, Fitchburg, WI (US); Bhavik Shah, Madison, WI (US); Larry G. Irwin, II, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 313 days.

(21) Appl. No.: 12/557,968

(22) Filed: Sep. 11, 2009

(65) Prior Publication Data

US 2010/0070306 A1 Mar. 18, 2010

Related U.S. Application Data

(60) Provisional application No. 61/096,709, filed on Sep. 12, 2008.

(51) Int. Cl.
| | |
|---|---|
| *G16H 10/60* | (2018.01) |
| *G16H 40/20* | (2018.01) |
| *G06Q 50/24* | (2012.01) |
| *G06Q 50/22* | (2018.01) |
| *G16H 50/70* | (2018.01) |

(52) U.S. Cl.
CPC ............ *G06Q 50/24* (2013.01); *G06Q 50/22* (2013.01); *G16H 10/60* (2018.01); *G16H 50/70* (2018.01)

(58) Field of Classification Search
CPC ............................... G06Q 50/22; G06Q 50/24
USPC ............................................... 705/2, 3
See application file for complete search history.

(56) References Cited

U.S. PATENT DOCUMENTS

2005/0236474 A1* 10/2005 Onuma et al. ............... 235/382
2009/0177495 A1* 7/2009 Abousy et al. ............... 705/3

(Continued)

*Primary Examiner* — Maroun P Kanaan
(74) *Attorney, Agent, or Firm* — Boyle Fredrickson, SC

(57) ABSTRACT

A computerized system allows intercommunication of patients with respect to the treatment of their diseases. This system includes an electronic medical record database providing electronic medical records of a given set of patients as developed by healthcare professionals and linked to an anonymous identifier for each patient and a set of terminal devices accessible to the patients allowing for the electronic exchange of information through a display and data input device. A server system connects the anonymous medical record database and the terminal devices and executes a stored program to: (1) allow an authenticated connection by a given patient to the server system through a terminal device and associate the connection with an anonymous identifier; (2) permit authoring by the given patient of a patient site viewable on a terminal device incorporating medical records from the anonymous medical record database associated with the anonymous identifier; and (3) identify to the given patient other patient sites for other patients having shared medical conditions according to a predetermined clustering of data of the anonymous medical record database.

6 Claims, 3 Drawing Sheets

(56) References Cited

U.S. PATENT DOCUMENTS

2009/0265316 A1\* 10/2009 Poulin .................. G06Q 10/06
2011/0202370 A1\* 8/2011 Green et al. ..................... 705/3

\* cited by examiner

PATIENT COMMUNITY SYSTEM WITH ANONYMIZED ELECTRONIC MEDICAL DATA

CROSS REFERENCE TO RELATED APPLICATIONS

This application claims the benefit of U.S. Provisional Application No. 61/096,709, filed Sep. 12, 2008, hereby incorporated by reference in its entirety.

BACKGROUND OF THE INVENTION

The present invention relates generally to electronic medical records systems used by health care providers and, in particular, to a system promoting patient communities for support and education based on verified medical information.

Traditionally, a patient's source of medical information has been largely limited to his or her personal physician, articles in the popular press, and the advice of friends and relatives. The Internet has greatly increased the variety of medical information available to the public, providing websites dedicated to medical information of particular medical conditions providing information and resources to visitors about those conditions. These websites expand on articles that could have been found in the popular press. In addition, the Internet has provided "medical" social networking sites allowing patients to exchange views and information about their medical condition and their management of their health with respect to their condition. Websites like PatientsLikeMe.com provide a framework allowing patients with particular medical conditions to connect electronically in "social network" type environments roughly analogous to conventional social networks such as Facebook.com and MySpace.com.

One problem with such medical social networking sites, arising from a problem endemic to the Internet generally, is that the information provided by the site cannot be wholly trusted. While it is likely that most participants on such sites endeavor to provide accurate information, the participants may not fully remember, understand, or accurately describe their treatments or outcomes. Generally, the information disseminated by such sites is subject to a "self-selection" bias toward information from individuals who choose to participate in the site and who decide to be forthcoming about their problems and successes. And while it is likely that most participants in such medical social networks are genuinely affected with the medical conditions discussed, such sites present a strong temptation to marketers to market products under the guise of being of a fellow patient.

These social networks can be very helpful in providing psychological support to those who have a particular medical condition; however, even this benefit is weakened if there is significant doubt about the identity of the other participants. And while the information gleaned from such sites may be useful on an anecdotal basis, it cannot rise to the level of scientific data.

SUMMARY OF THE INVENTION

Patients represent an untapped resource in their zeal to learn about their diseases and treatments and to promote the benefit of others in the same position. Nevertheless, the medical community is currently far from being able to effectively utilize the benefits of this potential resource.

The present inventors have recognized that a variation on the medical social networking system could enlist this community to greatly increase information sharing both among patients and doctors. Critical to unleashing this sharing process is that the patients be able to present verifiable medical information about their conditions. Under a community with verified patient medical information, the level of trust and quality of information transfer is substantially increased, providing a more satisfactory experience to the patient and potentially allowing improved information to be attained by healthcare professionals as well.

In one embodiment, the present invention therefore provides a computerized system allowing intercommunication of patients with respect to the treatment of their diseases. This system includes an electronic medical record database providing electronic medical records of a given set of patients as developed by healthcare professionals and linked to an anonymous identifier for each patient and a set of terminal devices accessible to the patients allowing for the electronic exchange of information through a display and data input device. A server system connects the anonymous medical record database and the terminal devices and executes a stored program to: (1) allow an authenticated connection by a given patient to the server system through a terminal device and associate the connection with an anonymous identifier; (2) permit authoring by the given patient of a patient site viewable on a terminal device incorporating medical records from the anonymous medical record database associated with the anonymous identifier; and (3) identify to the given patient other patient sites for other patients having shared medical conditions according to a predetermined clustering of data of the anonymous medical record database.

It is thus one object of the invention to fundamentally transform medical social networking by allowing accurate and verifiable medical data and participants.

In a related embodiment, the invention provides a set of terminal devices accessible to the physicians allowing for the electronic exchange of information through a display and data input device and the server system communicating between the anonymous medical record database and the terminal devices to: (1) allow a searching by a given physician of the anonymous medical record database according to search criteria entered by the given physician to provide a search result of patients; and (2) allow communication by the given physician with at least one patient's physician for a patient in the search result using the anonymous identifier to the patient's physician.

It is thus one object of the invention to greatly improve the quality of information transfer among patients in a way that promotes a general benefit to the medical community.

These particular objects and advantages may apply to only some embodiments falling within the claims and thus do not define the scope of the invention.

DETAILED DESCRIPTION OF THE INVENTION

Figure 1:
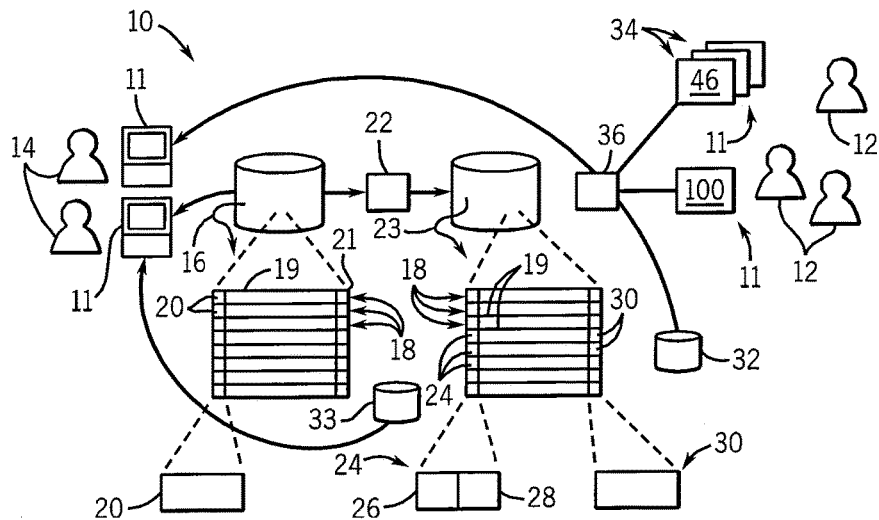
FIG. 1 is a block diagram of the system of the present invention providing medical social networking among patients based on actual electronic medical records.

Referring now to FIG. 1, the present invention provides a social networking system 10 for patients 12 and their physicians 14 using terminals 11 and making use of electronic medical records 16 holding medical data collected by healthcare professionals and thus having the highest level of trustworthiness. Generally the electronic medical records 16 will include many logical records 18 each associated with patient identification data 20 uniquely identifying a particular patient. The patient identification data 20 may, for example, be a number or an index value of the record 18 but is logically keyed to information allowing personal identification of the patient.

The data fields 19 of the electronic medical records 16 may include, for example, the patient's name, age, gender, as well as medical information such as height, weight, blood pressure, medical history, the results of lab tests, diagnoses by physicians, treatment outcomes, and the like. Included in the data fields 19 is information normally not freely available to the public and protected under federal standards such as the Health Insurance Portability and Accountability Act (HIPAA).

The physicians 14 may communicate with the electronic medical records 16 as is understood in the art during the course of their practice to update the data in the electronic medical records 16 and to use that data for their treatment of the patient informing diagnoses and recommendations. The electronic medical records 16 may provide for a primary physician field 21 indicating the patient's primary physician.

In the present invention the data of the electronic medical records 16 may be received by an anonymizer 22 which copies the data from the electronic medical records 16, on a periodic basis or as a "mirror" triggered by changes of the data of the electronic medical records 16, into an anonymized database 23. The anonymized database 23 also has records 18 with a one-to-one mapping with the records 18 of the electronic medical records 16. The difference between the anonymized database 23 and the electronic medical records 16 is that the patient identification data 20 is removed and replaced with an anonymous patient key 24 that can only be interpreted by the patient 12 and his or her physician 14. In a preferred embodiment, the anonymous patient key 24 is not linked to a personally identified patient by any information in the anonymized database 23.

In one embodiment, the anonymous patient key 24 may consist, logically, of a system-selected identification number 26 and a personal identification number (PIN) 28 provided to the patient 12. This personal identification number may be created, for example, by the patient him or herself through an authentication process in which the patient 12 is provided with a temporary PIN 28. The patient may then identify him or herself using the temporary PIN 28 and identifying information known by the patient, for example a Social Security number, to allow the patient to select an arbitrary PIN 28 to be used. It will be recognized that the system-selected identification number 26 and PIN 28 need not be contained in the record 18 but are logically linked to each record 18.

Patients who have not registered or obtained a PIN 28 will still have records in the anonymized database 23 but they will not be associated with PIN 28 indicating simply that the patient has not registered to produce a webpage or participate in medical social networking as will be described below. The anonymized database 23 include records from multiple medical institutions including from electronic medical records 16 having different record formats, the latter through the use of a remapping process of the type known in the art.

The anonymized database 23 also provides for each record 18 an anonymous physician key 30 that, like the anonymous patient key 24, cannot be linked to a personally identifiable physician by any data in the anonymized database 23. Each anonymous physician key 30, however, may be linked to an electronic contact address for that physician 14, for example an anonymous e-mail address, by a contact database 32 mapping the anonymous physician key 30 to an electronic address and, in the preferred embodiment, separate from the anonymized database 23.

While in the preferred embodiment, the anonymized database 23 provides no data that would allow personal identification of patients 14, as will be described in more detail below; in one embodiment, a separate one-way, cross-reference database 33 may be generated linking anonymous patient keys 24 to patient identification data 20 only for the patient's physician. In particular, this one-way, cross-reference database 33 will only be accessible to physicians and will only allow this cross-referencing process for a physician who is an attending physician for the particular patient. The one-way, cross-reference database 33 thus does not allow a general identification of patients. As will be described further below, the present invention allows data from the anonymized database 23 to be displayed on patient personal webpages 34 to be viewed by an authorized patient 12 and other authorized patients 12. Importantly, because the system-selected identification number 26 is not visible during the cross-referencing process, the one-way, cross-reference database 33 does not allow even the patient's attending physician to identify the webpages of their patients or link a particular webpage to a particular patient, preserving absolute anonymity of the patient in these activities.

Figure 6:
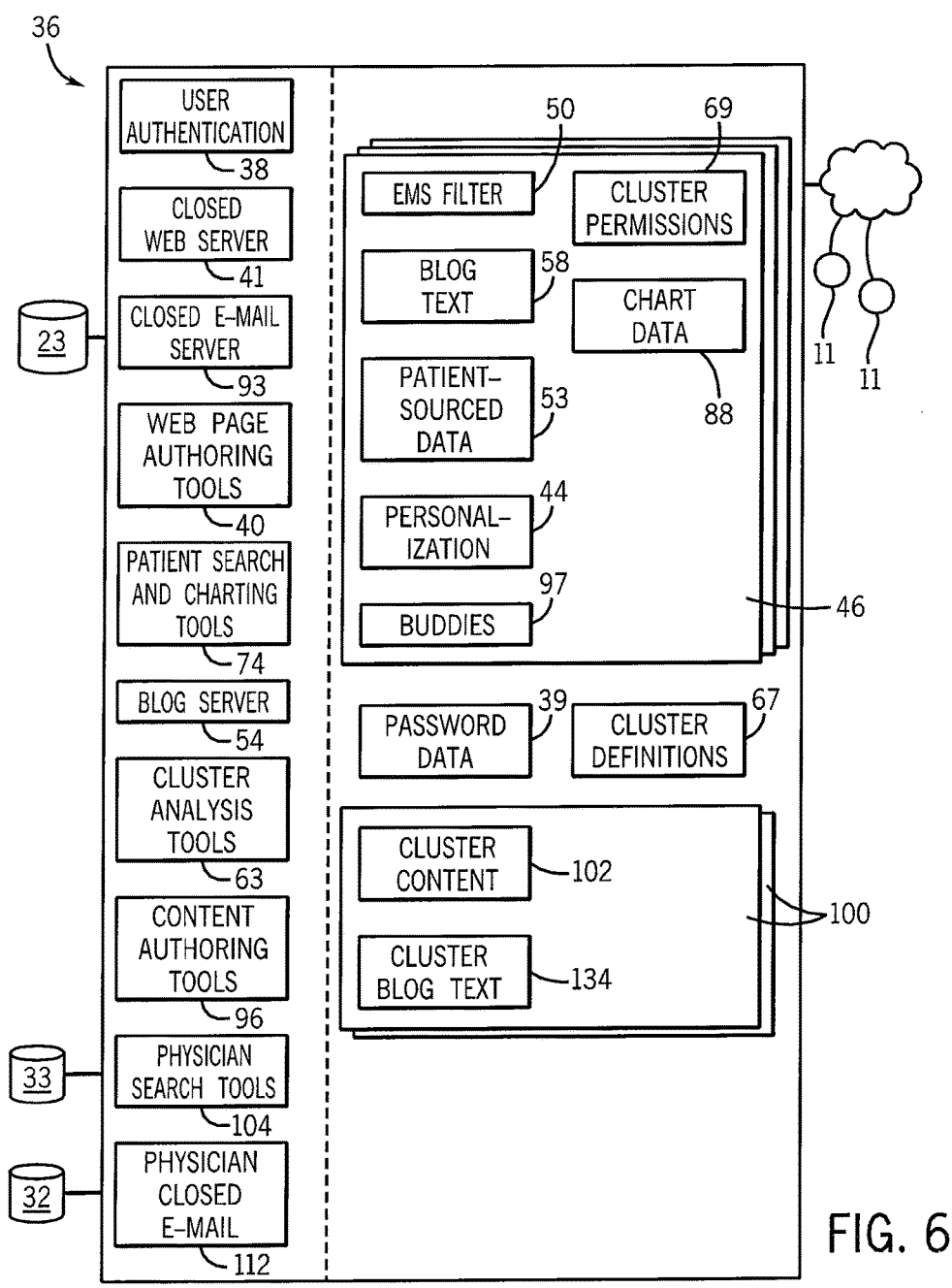
FIG. 6 is a logical diagram of the services and data structures used by the present invention.

Referring now to FIG. 6, the data of the anonymized database 23 may be processed by services in one or more server systems 36 (being electronic computers executing stored programs) to provide for viewing, sharing, and analyzing of the data of the anonymized database 23.

The server system 36, as a starting matter, provides for a closed community of physicians and patients through the use of a high-level patient authentication service 38 ensuring that users of the server are both authorized and validated as to their identity. This authentication service 38 may be part of the process in which the patient 12 is assigned a username mapped to the system-selected identification number 26 and a PIN 28 as described above. Together the usernames and PINs 28 are stored in a globally accessible password database 39. Services, as is understood in the art, are computer programs stored in computer readable medium for execution on an electronic computer.

Figure 2:
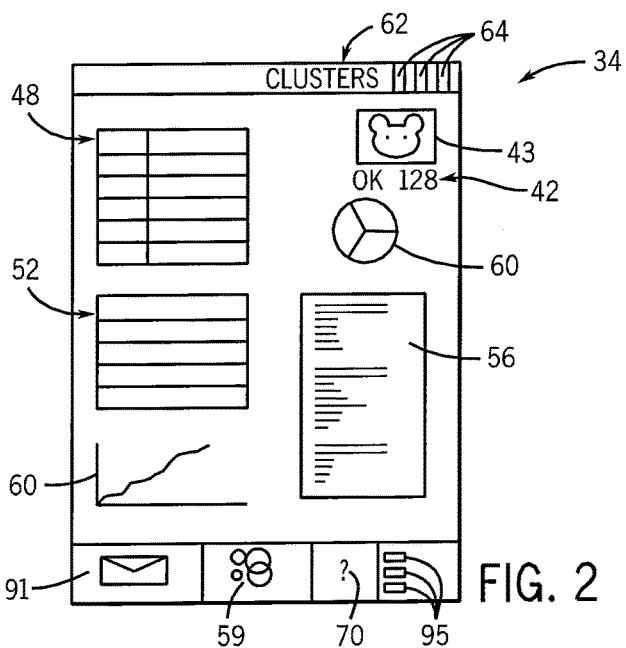
FIG. 2 is an example patient webpage generated using the system of FIG. 1 and incorporating medical record data.

Referring now also to FIG. 2, for authenticated users, the server system 36 provides for Web authoring tools 40 to allow the patient 12 to generate a webpage 34. The webpages 34 will be served by a Web server program 41 only to the closed community of authorized patients whose records are held in the anonymized database 23 to be visible only to patients 12 that have authentication service 38. Such a closed web community, for example, may be enforced by short-term cookies placed on the patient's browser after registration is complete and a security checking process occurs upon the loading of each Web page. In this way, the pages may also be blocked from scanning by search engine spiders.

The authoring tools 40 allow the registered patient to create a webpage in alias 42 (distinct from the username) and avatar 43 preserving absolute anonymity of the patients 12. The alias 42 may be automatically checked to make sure it does not match another alias or an actual patient name unless it is the patient's own name. This latter feature allows the patient 12 to reveal his or her identity but prevents a patient 12 from assuming another patient's identity. In addition the authoring tools 40 allow selection of the contents of the webpage 34 as well as background colors and arrangement of content. For patients who wish to reveal their identity, the avatar 43 may be replaced with a photograph. This personalization maybe stored in a personalization file 44 associated with a web-page data space 46 for that webpage 34.

Referring still to FIG. 2, importantly, the webpage 34 may have a medical record data block 48 providing data directly from the anonymized database 23 associated with the particular patient 12. This data maybe subject to translation from medical terminology to conventional English to improve its accessibility to the layperson, but is otherwise identical to the data stored in the medical record 16. The translation may be done automatically, for example, through a translation table (not shown) providing standard synonym relationships.

While the medical record data block 48 is indicated to be and verifiably contains actual medical information for the patient 12, the patient 12 is provided with the ability to select what medical information (fields) to reveal. In this regard, the patient 12 may select data to display and implement that selection through an EMS filter 50 held in the web-page data space 46 of the webpage 34. A data selection webpage (not shown) may be provided to the patient for this purpose allowing the selection of fields of data, for example, using a checkbox system. For participation in certain clusters, as will be described below, there may be an obligation to display certain information, and thus the patient's ability to filter using the EMS filter 50 may be constrained by membership rules as desired. These rules will generally require display of information only if the patient 12 wishes to join a particular cluster of patients and thus does not require the patient to reveal information as a general matter. The medical record data block 48 may include disease diagnoses, lab tests, treatments, and even patient demographic information.

In the manner of a conventional "personal health page", the webpage 34 also provides for patient-sourced data 52. This patient-sourced data 52 may include other information about the patient including medical facts as well as personal information such as hobbies, geographic location, etc. The patient-sourced data 52 is stored in a data file 53 in the web-page data space 46.

Referring still to FIGS. 2 and 6, blog server 54 allows the patient 12 to place a personal blog 56 (text log) on their webpage 34 (or linked from the webpage 34) with blog text stored persistently in blog file 58 associated with the web-page data space 46 according to generally understood techniques. Again, the blog 56 may be viewed only by registered patients per authentication service 38 and patients who have obtained the address of the webpage 34 as will be described below. In addition the patient may display one or more charts 60 whose generation will be described.

Figure 3:
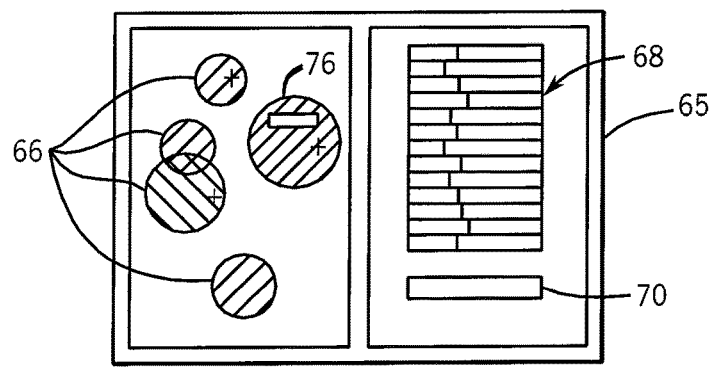
FIG. 3 is an example cluster display accessible by the patient from the webpage of FIG. 2 providing the patient with a selection of predefined clusters based on the patient's medical records.
Figure 4:
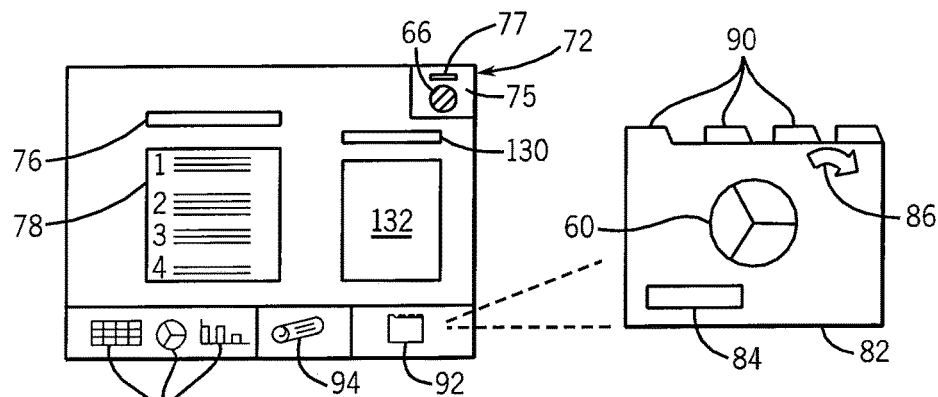
FIG. 4 is an example cluster home page for a particular cluster permitting a search of cluster members by a patient and providing analysis tools for the patient and access to other cluster-specific content.

Referring now to FIGS. 2, 3, and 6, once the patient has completed his or her webpage 34 it may be published in one or more clusters which the patient may join. Generally a cluster will be other patients having similar medical data who form a community for the patient 12. The patient 12 may select multiple clusters which become a searchable term for the patient's webpage 34 and which can be displayed in a display box 62 at the top of the webpage through a series of cluster icons 64 linked to cluster definitions.

The process of joining a cluster may be initiated, for example, by pressing a cluster button 59, upon which the patient 12 is presented with a cluster screen 65 generated by a cluster service 63 in the server system 36. Generally the cluster service 63 reviews registered patients and, through either or both of an automatic cluster analysis of a type known in the art, or by manual cluster creation by hospital staff, creates a set of clusters 66 indicated here as circular regions sized to show the number of members in the cluster and arranged roughly to show the relationship of the clusters 66 to each other with respect to similarities of underlying data. In this respect the clusters 66 are arbitrary groupings of multidimensional data in a multidimensional space where the multiple dimensions of data are data of the anonymized database 23. Thus, for example, the cluster 66 may be simply patients 12 with a certain disease type, this being a cluster 66 along a single dimension. More typically clusters will look at multiple dimensions of: disease types, ages, and gender, with the patient 12 having the ability to choose between larger superset clusters (for example disease type) or sub clusters, (for example of age and gender). Combinations of diseases may also form clusters 66 and the patients 12 may be allowed to suggest or create clusters 66 of their own.

Each cluster 66 may be selected by manipulation of a cursor upon which average cluster data 68 may be displayed to provide an indication to the patient 12 of the parameters of that particular cluster. In addition the cluster may be given a simple moniker 77 which may also be displayed in the circle of the cluster 66. Generally, although the patient 12 may belong to multiple clusters 66, in general, a patient may not belong to a cluster 66 unless the data of their record 18 of the anonymized database 23 fits the cluster definition. This data of the record 18 will be all the data of their record and typically not just the medical record data block 48. In this way patients 12 within a cluster 66 can be assured that the other patients 12 of that cluster 66 share similar characteristics per the cluster definition. It is believed that this ability to verify cluster membership will provide a better sense of community and promote improved sharing of information. For this reason, the publication of the user's webpage 34 may be limited to members of the clusters 66 they have joined. The patient's 12 cluster memberships are stored in a cluster file 69 in the web-page data space 46 while the clusters' definitions (being ranges of data within fields defining the cluster 66) may be stored in a cluster definition file 67 in the server system 36, both globally accessible.

Referring again to FIG. 2, a patient 12 may search for other users within a cluster that they have joined using a search tool invoked by search button 70 and invoking a search screen 72 generated by patient search service 74. This patient search service 74 provides simple searching tools, for example text searches for text strings on a particular webpage 34, within a selected cluster 66 displayed in a cluster control 75 in the corner of the search screen 72. The cluster control 75 may be "pressed" allowing the patient 12 to cycle through his or her clusters 66. Searching may be conducted preferably by a free text searching system having a text entry block 76 allowing the searched text to be entered along with field identifiers designating desired particular EMS fields 19 as well as values or ranges, or other elements (such as the blog 56). Generally, the search tools will permit searching only through the revealed medical record data block 48 for each webpage 34, but will allow unrestricted searching of any revealed information on the webpage 34 such as alias 42, blog text file 58, and the like. The search results may be provided in a search result box 78 ranked in order of closeness of match according to well-known algorithms such as those used in conventional search engines.

The patient search service 74 also provides data capture and charting utilities 80 allowing the patient 12 to capture search results and to present them in a tabular form or as various charts. For example, the patient 12 may wish to create a chart showing what medicines other patients in his or her cluster 66 are using, or how many members are of a certain age, or the like. Invoking one of the charting utilities opens a charting window 82 having controls 84 of the type well known in the art with respect to spread sheet programs to allow generation of the desired chart 60. For this purpose, the search results of search result box 78 may be tagged, for example, with XML tags allowing ready classification.

This generates charts 60 that may be imported into the patient's webpage 34 as described above. Generally the patient searches will be limited to clusters to which they belong, but not necessarily to patients that have registered or have created webpages 34. Simple surveys may be created for other patients in the clusters 66.

Charts 60 may also be generated from patient source data, for example with the patient tracking his or her compliance with a program or symptoms or the like. The charts 60 may, in this case, provide a method for a patient to track his or her progress and communicate that progress to other patients who may be supporting them. Charts of this type, as well as questionnaires provided by a physician to a cluster 66, may provide a valuable point of patient sourced data that may be used by physicians 14 as described below. Of particular importance may be patient-sourced information related to the patient's perception of outcome of their treatment.

The chart 60 and the underlying data may further be captured and forwarded to a physician through an e-mail button 86 allowing the patient to share observations with his or her physician or other members of the cluster 66. Multiple chart types may be captured and saved in a file in the chart data file 88 stored in the web-page data space 46 to be accessible at a later time by the patient through, for example, tabs 90 on the charting window 82. Saved charts may be invoked through a patient-record button 92 or the like.

The search screen 72 may also provide a connection to cluster-based information related to the displayed cluster 66 in the cluster control 75 through news button 94 providing a link to useful information prepared by the system administrator using content authorization tools 96. This news may be recent developments in treatment, or helpful tips and suggestions targeted to members of that cluster 66. This news may, for example, be used to recruit volunteers for studies and more information from members of the cluster. News headlines may be displayed on the charting page in a headline block 130 and this content may be stored in a cluster data block 100 as cluster content data 102. The cluster page may also provide for cluster specific discussion groups and blogs 132 contained in cluster blog data 134 associated with cluster data block 100.

Referring again to FIG. 2, the patient may also press a contact button 91 to invoke a closed e-mail service 93 allowing the patient 12 to contact other patients using their aliases 42. Particular patients may have other patients in aliases enrolled in a buddy list 95 displayed on the webpage 34 providing a fast method of contacting these patients through closed e-mail or visiting their pages and allowing other viewers to network through the patient's webpage 34 such as provides a list of associations. The buddy list may be stored in a file 97 in the patient's webpage web-page data space 46. While not shown, an instant messaging type service could also be provided.

Figure 5:
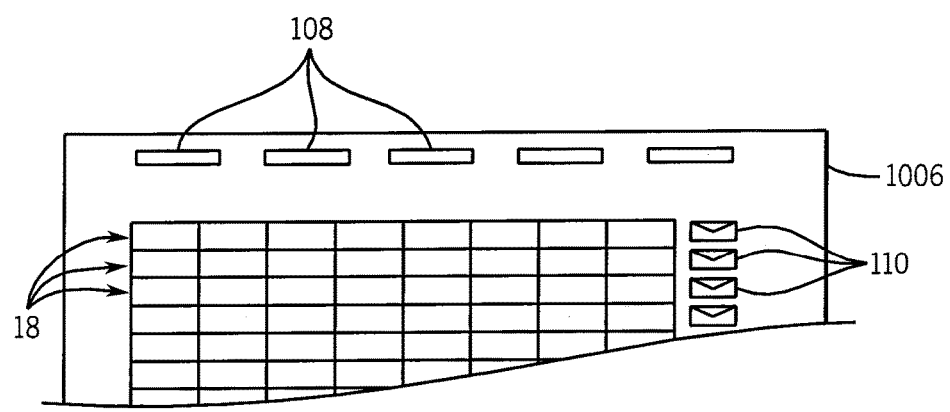
FIG. 5 is an example physician page providing for more sophisticated search tools for physician searching and analysis of the anonymous medical record data.

The anonymized database 23 and the patient source data provide a tremendous opportunity to physicians to obtain additional information from a large cohort of patients. Thus, the server system 36 provides physician search tools 104 that may be invoked, for example, as shown in FIG. 5 via a search page 106. Generally this search page 106 will provide much more sophisticated search tools providing multifield search boxes 108 that may be linked in Boolean combinations within or outside of an individual cluster 66. The revealed data records 18 may be exported to analysis programs or analyzed using charting and other statistical processing tools contained in the physician search tool service 103. Each record 18 revealed in a search will be associated with a contact icon 110 allowing the physician to contact the physician of the particular patient without knowing the patient's identity. Contact icon 110 employs a physician closed e-mail service 112 using the contact database 32 and provides an e-mail to a physician of the anonymous patient using the closed e-mail service 112. This e-mail permits the searching physician to contact the physician of a patient identified in the search allowing the searching physician to ask for more information about the patient in a physician-to-physician exchange. The physician receiving the e-mail is provided a link managed by the closed e-mail service 112 allowing the physician receiving the e-mail to identify the patient who is the subject of inquiry by name without revealing the system-selected identification number 26 or the patient's alias 42. In this way the anonymity for other patients 12 is preserved as well as the anonymity of the particular webpage 34 for the patient being discussed. The closed e-mail service 112 may be useful for a doctor looking for treatment options for a patient having an unusual set of conditions allowing the physician to identify other physicians who may have useful information about patients under their care. Note that at no time does the patient's physician need to reveal the patient's actual identity providing improved privacy for the patient. It should be emphasized that for many interesting types of studies, the anonymized database 23 will be sufficient since it contains validated medical data.

A physician may also register in the same manner as a patient 12, but for a physician-only cluster 66, allowing the same tools available to the patients to be also provided to the physicians in a separate section not accessible by the patients thus allowing physicians to provide physician interest groups per clusters of diseases defined according to the patient data, and to prepare blogs and the like for the sharing of information. Of course, a physician may also register within the patient clusters as a physician (and thus not need to reveal their own medical data) to be available to the cluster as a resource to ask questions or the like.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A computerized system allowing intercommunication of patients with respect to the treatment of their diseases comprising:
   an electronic medical record database providing electronic medical records of a set of patients as developed by healthcare professionals, each electronic medical record including patient identification and patient health data, the patient health data in electronic medical records being updated by the healthcare providers in the course of treatment of a patient informing diagnoses and recommendations;
   an anonymous electronic medical record database including anonymous patient records, where each anonymous patient record includes a copy of the patient health data from a copied electronic medical record of the electronic medical record database, an anonymous patient key that is linked to the patient identification of the copied electronic medical record of the electronic medical record database and an anonymous physician key linked to a physician identified in the copied electronic medical record of the electronic medical record database;
   a set of terminal devices accessible to the patients allowing for the electronic exchange of information through a display and data input device;
   a server system communicating between the anonymous electronic medical record database and the terminal devices and executing the stored program contained in computer readable memory to:
   (1) receive a connection request from a given patient to the server system through a terminal device including the anonymous patient key and a PIN provided to a patient identified by the patient identification of the copied electronic medical record of the electronic medical record database;
   (2) receive instructions from the given patient to generate a patient site, the created patient site incorporating medical records from the anonymous medical record database associated with the anonymous patient key;
   (3) identify one or more patient medical conditions based on the anonymous medical records;
   (4) identify to the given patient a cluster of other patient sites for other patients having medical conditions matched to the identified patient medical conditions listed in the anonymous patient record linked to the anonymous patient key;
   (5) receive a selection of at least one identified cluster;
   (6) receive a request to publish the patient site to the at least one identified cluster;
   (7) update the cluster to include the patient site such that response to subsequent cluster requests will include the generated patient site; and
   (8) receive cluster functionality instructions based on the identification of the patient site as being in the patient cluster.

2. The computerized system of claim 1, wherein the copied patient health data from the electronic medical records are a selection of one or more data fields of the patient health data from the copied electronic medical record.

3. The computerized system of claim 2, wherein the data field selection of the patient health data incorporated into the patient site is defined by the patient associated with that electronic medical record.

4. The computerized system of claim 2, wherein the data field selection of the patient health data is defined by a predetermined clustering of data associated with a shared medical condition.

5. The computer system of claim 2, wherein access to other patient sites for other patients having shared medical conditions for a patient is granted based on a determined match between a patient medical condition in the copied patient health data selected to be copied to the patient anonymous medical record related the shared medical condition.

6. The computerized system of claim 1, where each cluster of other patient sites is associated with a plurality of parameters and matching the identified patient medical conditions listed in the anonymous patient record linked to the anonymous patient key includes matching those parameters to the identified patient medical conditions.

* * * * *